United States Patent [19]

Pallas et al.

[11] Patent Number: 6,060,522

[45] Date of Patent: May 9, 2000

[54] SURFACTANT CO-CLATHRATES

[75] Inventors: Norman Robert Pallas, Freehold, N.J.; James Lyle Hazen, Galloway, Ohio

[73] Assignee: Rhodia Inc., Cranbury, N.J.

[21] Appl. No.: 08/911,123

[22] Filed: Aug. 14, 1997

[51] Int. Cl.$^7$ .......................... B01F 17/42; B01F 17/54; C07C 275/02

[52] U.S. Cl. .................... 516/102; 71/64.13; 71/DIG. 1; 252/363.5; 504/116; 514/952; 564/1.5

[58] Field of Search ........................ 516/102; 71/DIG. 1; 504/116; 514/952; 564/1.5; 252/363.5

[56] References Cited

U.S. PATENT DOCUMENTS

| | | | |
|---|---|---|---|
| 2,520,716 | 8/1950 | Fetterly | 564/1.5 |
| 2,569,984 | 10/1951 | Fetterly | 564/1.5 |
| 2,665,256 | 1/1954 | Barker | 564/1.5 X |
| 3,299,112 | 1/1967 | Bailey et al. | 556/445 |
| 3,562,786 | 2/1971 | Bailey et al. | 516/18 |
| 3,886,125 | 5/1975 | Chromecek | 71/DIG. 1 |
| 4,908,208 | 3/1990 | Lee et al. | 504/116 X |
| 4,933,002 | 6/1990 | Petroff et al. | 71/DIG. 1 |
| 5,017,216 | 5/1991 | Petroff et al. | 71/DIG. 1 |
| 5,059,704 | 10/1991 | Petroff et al. | 556/437 |
| 5,104,647 | 4/1992 | Policello | 514/772 |
| 5,145,978 | 9/1992 | Petroff et al. | 556/437 |
| 5,558,806 | 9/1996 | Policello et al. | 71/DIG. 1 |
| 5,705,690 | 1/1998 | Varadaraj et al. | 564/1.5 |

FOREIGN PATENT DOCUMENTS

| | | |
|---|---|---|
| 2093377 | 4/1993 | Canada . |
| 242592 | 4/1969 | U.S.S.R. . |
| WO89/12394 | 12/1989 | WIPO . |
| WO94/22311 | 10/1994 | WIPO . |

OTHER PUBLICATIONS

J. Radell and P.D. Hunt, "Occlusion of Organosilanes by Urea", *Journal American Chemical Society*, vol. 80, pp. 2683–2685 (1958).

R. Davis, "Solid Adjuvants Based on Urea–Surfactant Adducts", A Presentation on Behalf of I.C.I. Americas, Inc., Wilmington, DE. (1993).

F. E. Bailey, Jr., and H. G. France, "Molecular Association Complexes of Polymers. Urea and Thiourea Complex of High Molecular Weight Poly(Ethylene Oxide)", *Journal of Polymer Science*, vol. 49, pp. 397–406 (1961).

L. Mandelcorn, "Clathrates", *Chemical Reviews*, vol. 59, pp. 827–839 (1959).

L. C. Fetterly, "Study of Kinetic and Equilibria of Urea–Fatty Acid and Related Complexes", PhD. Thesis, Univ. of Washington, Seattle (1950).

E. Makin, "Clathration", *Encyclopedia of Chemical Technology*, vol. 6, pp. 179–189 (John Wiley & Sons, New York, N. Y.) (1979).

V. D. Simonov, et al., "Use of Clathrate Compounds of Urea With Surfactants in the Production of Pesticidal Preparations", *Dokl. Neftekhim. Sekts. Bashkir. Respub. Pravl. Vses. Khim. Obshchest.* 6:326–9, 15 (1971) From: Ref..ZH., Khim. 1972, Abstr. No. 4N648. [Translation Enclosed].

L. Jansen, "Enhancement of Herbicides by Silicone Surfactants", *Weed Science*, vol. 21, Issue No. 2, pp. 130–135 (Mar. 1973).

B. Hardman and A. Torkelson, "Silicones", *Encyclopedia of Polymer Science and Engineering*, vol. 15, pp. 204–308 (John Wiley & Sons, New York, N. Y., 1989).

(List continued on next page.)

*Primary Examiner*—Richard D. Lovering
*Attorney, Agent, or Firm*—John Daniel Wood

[57] ABSTRACT

A solid, water-soluble complex comprising:

a) a polysiloxane of the formula:

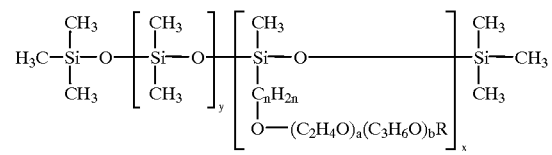

wherein n is from 2 to 6; a is from 8 to 25; and b is from 0 to 25; and the oxyalkylene groups may be random or block mixtures; y is from 0 to 5; x is from 1 to 5; and R is selected from the group consisting of hydrogen, $C_1$–$C_4$ alkyl, and a $C_1$–$C_4$ alkyl ester; or

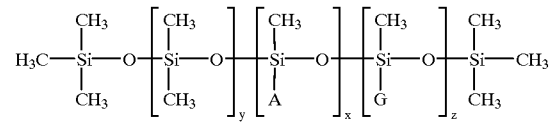

wherein A is a linear or branched alkyl having 6 to 30 carbon atoms; G is a glycol moiety of the formula —R'(OCH$_2$CH$_2$)$_m$ OR" wherein R' is a divalent alkylene group having 2 to 6 carbon atoms; R" is selected from the group consisting of hydrogen, $C_1$–$C_4$ alkyl, and a $C_1$–$C_4$ alkyl ester; m is 8 to 100; y is 0 to 5; X is 0.1 to 2.5; and z is 0.1 to 5.0;

b) a complex-forming agent of the formula:

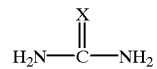

wherein X is O, S, Se, or Te, and c) a readily clathratable polyoxyethylene, e.g. a tridecyl alcohol ethoxylate having eight or more oxyethylene units.

These complexes are useful as adjuvants for dry agricultural chemicals such as pesticides and/or fertilizers. The complex may also contain a non-clathratable polyoxyethylene, e.g. a block copolymer of ethylene oxide and propylene oxide having a ratio of ethylene oxide to propylene oxide of not more than about 0.87:1.

45 Claims, 8 Drawing Sheets

OTHER PUBLICATIONS

"Silicones for the Agricultural Industry", Union Carbide Technical Brochure, pp. 1–24. (Jun. 1984).

H. M. Powell, "Clathrates", *Non–Stoichiometric Compounds,* Chapter 7, pp. 439–489, (Academic Press, Inc., New York, N.Y., 1964).

L. C. Fetterly, "Organic Adducts", *Non–Stoichiometric Compounds,* Chapter 8, pp. 491–567, (Academic Press, Inc., New York, N.Y., 1964).

L. A. K. Staveley, "Physics and Chemistry of Inclusion Complexes", *Non–Stoichiometric Compounds,* Chapter 10, pp. 607–635, (Academic Press, Inc., New York, N.Y., 1964).

SURFACTANT CO-CLATHRATES

FIELD OF THE INVENTION

This invention relates to dry silicone products and methods for preparing same. These solid, free flowing water-soluble complexes are especially useful as adjuvants for dry agricultural chemicals such as pesticides and/or fertilizers.

BACKGROUND OF THE INVENTION

Silicone surfactants, or more properly, organosilicones exhibit unusual properties that account for their use in a large number of specialty applications. For example, many have excellent wetting and penetrating characteristics.

The term silicone denotes a synthetic polymer which contains a repeating silicon-oxygen backbone and has organic groups attached to a significant proportion of the silicon atoms by silicon-carbon bonds. In commercial silicones, most R groups are methyl, higher alkyl, fluoroalkyl, phenyl, vinyl, and a few other groups substituted for specific purposes; e.g., hydrogen, chlorine, alkoxy, acyloxy, and alkylamino.

Commercially useful silicone products are usually made by the process whereby silica is catalytically reacted with an RCR group which is usually methyl chloride. Hydrolysis of the organochlorosilanes formed yield the siloxane structures which are the bases of many silicon products as outlined in the reaction scheme I.

$$2R_2SiCl_2 + 4 H_2O \rightarrow 2[R_2Si(OH)_2] + 4 HCl$$

(Unstable)

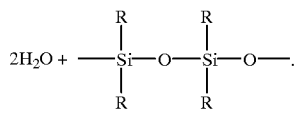

I

The three commercially important classes of silicone polymers include silicone homopolymers, silicon random copolymers, and silicone-organic (block) copolymers. Polydimethylsiloxanes (II) constitute by far the largest volume of homopolymers produced today.

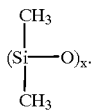

II

Polydimethylsiloxane is usually the principal component of the random copolymers and the principal siloxane building block or component of most silicone-organic copolymers.

The molecular weight of the polysiloxanes is usually controlled by the chain terminating groups. The trimethylsiloxy group from hexamethyl disiloxane (III) results in polymers that do not polymerize further by chain extension.

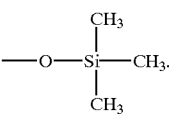

III

In fact, the first known silicones are the trimethylsiloxy-terminated siloxanes. The properties of these siloxanes are modified by substitution of the methyl groups on the silicon atom in the —Si—O— backbone by hydrogen, alkyl, phenyl, or organofunctional groups.

Structurally, organosilicones derive their apolar (hydrophobic) properties from the silicon-based rather than carbon-based moieties. Polar groups, such as ethylene oxide chains, can be introduced into copolymers to provide enhanced hydrophilic properties. Common silicone surfactants are derivatives of monomethyl and dimethyl silicone compounds which are conjugated with ethylene or propylene oxide chains (glycols) or with substituted aliphatic carbon moieties containing amino or carboxyl substituents.

As a result of the weak intermolecular forces and the very high flexibility and rotational freedom that exist on the backbone of these polymers, linear siloxanes have very low melting points, do not crystallize under ordinary conditions; and, in fact, many are liquid at room temperatures.

As mentioned above, silicones have an unusual array of properties. Chief among these are thermal and oxidative stability and physical properties little affected by temperature. Other salient properties include resistance to weathering, ozone, and radiation; low surface tension; high surface activity; good spreading power; and, when unmodified, being chemically and biologically inert.

Nonionic surfactants are commonly used as agricultural adjuvants to improve the efficacy of pesticides such as herbicides, fungicides, growth regulators, biologicals, and micronutrients. The surfactants play several roles in these agricultural formulations. For example, as activator agents, they can enhance the biological effectiveness of a pesticide. As a compatibility agent, they can selectively reduce or eliminate undesirable chemical interactions of two or more agrochemicals in a formulation and/or improve homogeneity of, for example, fertilizer with other agrochemicals in the mixture. As wetting or spreading agents, they increase the surface area covered by a given volume of the agricultural formulation. This is especially important for the spreading of solutions on difficult to wet surfaces such as a waxy leaf cuticle. The nonionic surfactants also aid in the uptake of active ingredients into plant tissue through permeation of the cuticle, through defects in the surface, and in some special cases, through flooding of the leaf stomata. Urea, ammonium nitrate, diammonium phosphate, and diammonium sulfate are also often used as agricultural adjuvants to supply nitrogen to crops and often, serendipitously to enhance the biological efficacy of pesticide formulations.

Certain organosilicone compounds have bene recognized as excellent agricultural adjuvants, because of their outstanding wetting characteristics, enhancement of foliar uptake, and unique ability to increase the overall bioefficacy of many pesticide formulations especially those formulations containing glyphosate as the primary active.

Most of the organisilicone adjuvants, however, have the distinct disadvantage of being liquids, pastes or soft waxes at ambient temperatures. Thus, they are extremely difficult to include uniformly in dry pesticidal formulations. Attempts to overcome this liquid problem have utilized various adsorbents such as clays or silicas as solid carriers. However, these solid carriers are not soluble in water, not biologically active, clog fine spray lines and nozzles, and increase nozzle wear. Often, the surfactants are heated prior to blending to ease handling by decreasing viscosity which may, in turn, have a negative effect on its or the blend components chemical stability. In addition to the difficulties encountered in attempting to obtain uniform distribution of liquid surfactant in a powdered or particulate blend, the resulting tackiness oftentimes results in masses of material sticking to the walls of the blending apparatus.

In view of the above, it would be highly desirable to be able to produce agriculturally useful, organofunctional polysiloxanes in a dry state.

Clathrates, also referred to as inclusion complexes are single-phased solids consisting of two distinct components; with the molecule of one component being retained in closed cavities or cages provided by the crystalline structure of the molecules of the second component. The two components of a clathrate do not react chemically with each other, but the solid clathrates have sharp melting points.

A more recently explored class of inclusion complexes also known as tube, channel or canal inclusion complexes or adducts, form needle crystals and exhibit a lack of conformity to the classical law of simple multiple proportions. The most widely known examples of these non-stoichiometric complexes are the channel adducts of urea-n-paraffin, and thiourea-branched chain paraffins. The molecules of one component are bound together, usually by hydrogen bonds, to give rise to large tubular intertwining polymer networks in which the molecules of the second component may become entrapped, anchored, or stabilized. The compound which traps or encloses another molecule has become known as the host, and molecules which become enclosed are often called the guest molecules. These complexes form only as continuous crystalline lattices and, although they appear to lack conventional bonding, many of these complexes are quite stable. The host molecules molecularly encapsulate and thereby modify the apparent physical and chemical properties of the guest molecules. An unusual property of the organic channel adducts is that their stability depends in part upon a very exact fit within the tubular cavity or cavities which the host molecules can form; thus we are also dealing with substances which depend on the size and shape of the guest molecules for interaction.

Early work with n-paraffins found that urea and thioureas form the channel molecular inclusion complexes, that is, the urea and thiourea molecules form a hollow channel just large enough to accommodate the planar zigzag of the n-paraffin hydrocarbon molecule; essentially large interpenetrating helical spirals forming a nearly circular dimensioned, or hexagonal latticed channel with the hydrocarbon molecules at the center.

Urea by itself forms a tetragonal structure, however, a crystalline transformation to the hexagonal structure occurs when an inclusion complex is formed.

Among the straight chained hydrocarbons, n-hexane is the smallest member which has formed an inclusion complex with urea. In general, with any homologous series, the stability of the inclusion complexes, i.e., the ability to form a separable, dry precipitate, increases with the chain length of the guest molecule. Large end groups have a negative effect on the formation of channel complexes which often can be overcome by significantly increasing the length of the hydrocarbon chain being complexed.

A number of other n-aliphatic organic compounds, besides the straight paraffinic chains have been reacted with urea. Fatty acid series have been studied as well as inclusion complexes of the n-alcohols, esters, halides, diglycerides, dibasic acids, olefins, and many related normal aliphatic structures. Inclusion complex studies of homologous series involving maleate, fumarate, and fluorinated esters have been reported.

With each class of compounds or homologous series, there is a minimum chain length which is required for adduct formation. For n-paraffins, the minimum chain length is six carbons at room temperature and pressure, but under pressure and at lower temperatures, even propane can be made to react. There is no theoretical upper limit to the length of paraffin chains which will complex with urea. In fact, urea channel adducts have been formed by reaction with poly (ethylene oxide) polymers as high as 4,000,000 in molecular weight.

Clathrates are generally prepared by recrystallization and precipitation from solution. If the host is soluble in the guest component, the preparation is simple. Otherwise, it is necessary to use a common solvent which cannot be clathrated by the host. Water is typically the solvent of choice. Of course, in crystallizing solutions where the concentration of the guest component is low, stirring and slow crystallization are necessary to avoid depletion of the guest component at the site of crystallization after initial clathrate formation.

Radell and Hunt (J. Am. Chem. Soc. 80, 2683 (1958)) prepared urea inclusion complexes of three monoalkylsilanes and four dialkylsilanes and reported that the complexes were white crystalline solids with "the melting point of urea". They noted that although hexane is the shortest hydrocarbon molecule that will form a crystalline urea complex under normal conditions, neither amylsilane nor hexylsilane would form such a crystalline structure. Thus they concluded that although a single silicon atom per se in the backbone of a linear hydrocarbon chain does not prevent the formation of a urea inclusion complex, it has a destabilizing influence.

In 1993, R. Davis of ICI Surfactants presented a paper entitled Solid Adjuvants Based on Urea-Surfactant Adducts in which he proposed that certain agrochemical surfactants would be good candidates for urea complexation, i.e., for conversion into free flowing powders. Among those suggested were, polyethylene glycols; EO/PO block copolymers; and ethoxylated alcohols, acids, and nonyl phenols. Ethoxylated tridecyl alcohol was exemplified. Davis also proposed that once such urea-surfactant adducts were formed, other adjuvants could be added to change the adjuvant properties of the final product such as phosphate ester acidifying agents, ethoxylated silicone wetting agents, and various sticking agents.

Canadian Patent No. 2,093,377 (Chesin and Davis) discloses solid, free-flowing adjuvants comprised of a water soluble adduct of urea and at least one surfactant selected from the group consisting of an ethoxylated linear or branched chain aliphatic alcohol or acid having 8 to 24 carbon atoms and at least 10 moles of ethylene oxide per mole of alcohol or acid; block or random copolymers of ethylene oxide and propylene oxide; and block or random copolymers of ethylene oxide and propylene oxide based on aliphatic alcohols having 4 to 18 carbon atoms. Chesin and Davis not on page 7 that many surfactants, including many polyoxyethylenes were tried but were not compatible with urea, and/or do not produce complexes with urea or do not form satisfactory solid adducts.

L. C. Fetterly (Study of Kinetics and Equilibria of Urea-Fatty Acid and Related Complexes, Ph.D. Thesis, University of Washington, Seattle, 1950) suggested that linear silicon polymers probably do not form inclusion complexes because the chain diameter is too large. He, in fact, tried to prepare complexes of these polymers, as well as an inclusion complex of dichlorosilane from urea and thiourea and was unable to do so. Illustrative of the sensitivity of the inclusion complexes to the diameter of the guest molecule, Fetterly noted that whereas normally one can form a urea inclusion complex with an n-paraffin carbon chain of 6 or greater; a linear paraffin chain of almost 18 C-atoms in length is required to off-set the distortion caused by a single methyl group in the 2 position.

Since it is presently impossible in most instances to predict solid molecular crystalline structure a priori, the discovery of a new clathrate or clathratable material has been and still is a matter of chance.

OBJECT OF THE INVENTION

It is an object of this invention to prepare solid, free-flowing adjuvants from initially liquid ethoxylated polysiloxanes, optionally with other chemicals which are also difficult to clathrate.

It is also an object of the present invention to prepare solid, free flowing agricultural adjuvants from nonionic surfactants of proven bioefficacy which are 100% active; contain no water-insoluble carriers; provide excellent wetting properties and provide fertilizer activity.

It is another object of this invention to provide a dry, solid free-flowing fertilizer-surfactant powder which has low phytotoxicity, is environmentally friendly, has excellent handling properties and rapidly dissolves or disperses in water.

Other objects and advantages will be apparent from the descriptions and examples which follow.

SUMMARY OF THE INVENTION

Figure 1:
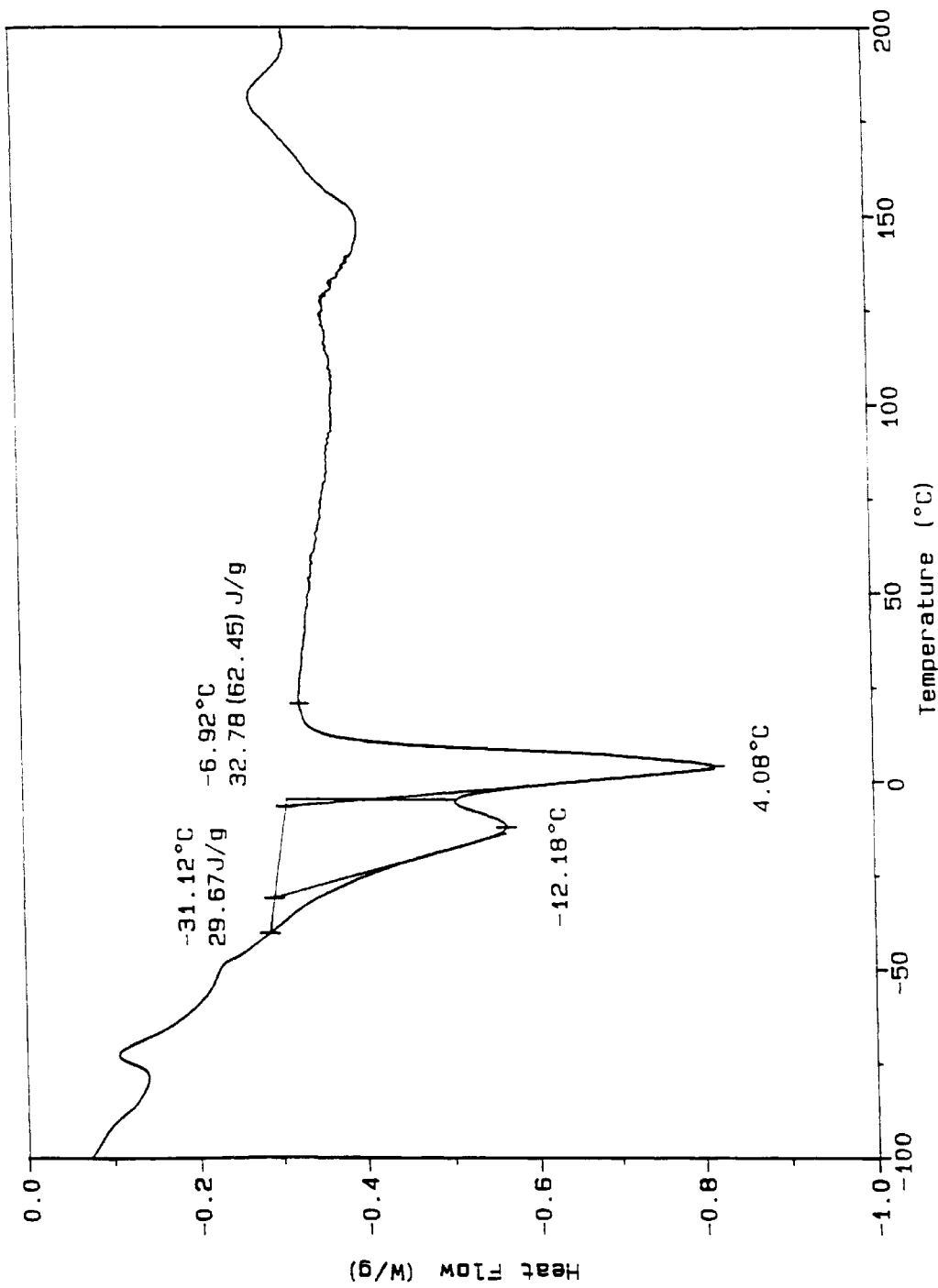
FIG. 1 is a graphic depiction of the results of a DSC scan of unclathrated SILWET L-77® polysiloxane.

The present invention relates to the discovery that certain chemicals which are non-clathratable, when co-clathrated with a readily clathratable chemical, can be prepared as dry, solid, free-flowing complexes. A "non-clathratable" chemical is one which is difficult to clathrate, i.e. the chemical does not form a clathrate with urea or forms clathrates with urea only at low percentages of the chemical, when subjected to a standard clathration process, e.g. organosilicone surfactants wherein the organic group has less than about 12 oxyethylene units and certain polyoxyethylenes. A "readily clathratable" chemical is one which readily forms a clathrate with urea, e.g. certain other polyoxyethylenes. It has been surprisingly found that significant amounts of non-clathratable chemicals can be used to form dry, solid, free-flowing complexes when co-clathrated with one or more readily clathratable materials.

In one aspect, this invention relates to a composition comprising a dry, solid, free-flowing complex of urea or an analogue thereof, a readily clathratable polyoxyethylene, and a non-clathratable organosilicone surfactant. Said organosilicone surfactant is typically present in an amount of greater than 0.3% by weight of said complex. Typically, the weight ratio of readily clathratable polyoxyethylene to non-clathratable organosilicone surfactant will range from about 166:1 to about 1:3, more typically from about 2:1 to about 1:2, and even more typically from about 1.5:1 to about 1:1.5. The weight ratio of the sum of the weights of the readily clathratable polyoxyethylene and the non-clathratable organosilicone to urea will typically range from about 3:2, to about 1:19, more typically from about 1.2:1 to about 0.82:1, and more typically from about 0.95:to about 1.05:1.

In another aspect, this invention relates to a composition comprising a dry, solid, free-flowing complex of urea or an analogue thereof, a readily clathratable polyoxyethylene, a non-clathratable organosilicone surfactant and a non-clathratable polyoxyethylene. The amount of the urea, or analogue thereof, as a percentage of the weight of the complex will typically range from about 70% to about 30%, more typically from about 60% to about 40%, and even more typically from about 45% to about 55%. The amount of the readily clathratable polyoxyethylene as a percentage of the weight of the complex will typically range from about 10% to about 40%, more typically from about 20% to about 30%, and even more typically from about 22% to about 26%. The amount of the a non-clathratable organosilicone surfactant as a percentage of the weight of the complex will typically range from about 5% to about 40%, more typically from about 10% to about 15%, and even more typically from about 11% to about 14%. The amount of the non-clathratable polyoxyethylene as a percentage of the weight of the complex will typically range from about 5% to about 40%, more typically from about 10% to about 15%, and even more typically from about 11% to about 14%.

The organosilicone surfactants are ethoxylated polysiloxanes and, in addition to providing fertilizer characteristics, the complexes prepared therefrom are excellent adjuvants for the agricultural delivery of solid fertilizers and pesticides such as micronutrients, biologicals, insecticides, herbicides, fungicides, and plant growth regulators. The non-clathratable polyoxyethylenes are typically surfactants which contain a hydrophobic group other than an organosilicone group and which contain a hydrophilic polyoxyethylene group.

The crystalline complexes of this invention may be formed by adding the chemicals to be clathrated, e.g. a readily clathratable chemical, an ethoxylated polysiloxane, and a non-clathratable polyoxyethylene surfactant, to a saturated solution of urea in water at elevated temperatures; lowering the solution temperature to crystallize the clathrate;

and evaporating the water. Optionally, the material can be ground to a fine powder.

These free-flowing adducts can be included into a dry pesticide formulation to improve wetting, compatibility, buffering, or other well known adjuvancy characteristics. Alternatively, these inclusion complexes, with their rapid dissolution properties, can be added directly to the spray tank or used like any other tank-mix adjuvant. Regardless of the method used, the adjuvants of this invention will activate pesticides biologically as well as function as wetting agents, compatibility agents or fertilizer-nutrients. Enhanced activity, biologically or otherwise, achieves the desired pesticidal effect with lower levels of the more expensive pesticide active. By "water-soluble", it is meant that the complex, when dispersed in water, will contribute to the dispersion no solid particles that can clog fine spray lines or nozzles or increase nozzle wear. Thus, "water-soluble" does not mean that all components must dissolve to form a true solution in an aqueous medium.

DETAILED DESCRIPTION OF THE INVENTION

The instant invention relates to the discovery that certain liquid organofunctional polysiloxanes, even though possessing multiple destabilizing silicon atoms; the extremely rotational and flexible Si—O—Si bonds; and very large end groups can be converted, along with non-clathratable polyoxyethylene surfactants, into a dry, free-flowing crystalline solid. The products of this invention are inclusion adducts or compounds of the complex-forming agents with ethoxylated polysiloxanes as described below. While the exact structures of these solid complexes are not known, it is believed that at least a physical combination exists. Evidence for the individual existence of a complex is found in the fact that the thermal transitions for the components is absent (or almost entirely so) from a DSC thermogram of the product while a new thermal transition, believed to be that of the product complex, appears in the DSC thermogram. In this detailed description, all amounts and all numerical values for repeating units should be understood to be qualified by the term "about", unless otherwise expressly noted in context. Further, it should be noted that while the numerical values for repeating units will be whole numbers for pure compounds, the numerical values will typically be represented by number which include fractional or decimal expressions which indicate an average value for a polydisperse mixture.

The complex forming agents are represented by the formula:

IV 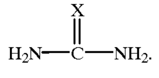 wherein X is O, S, Se, or Te; i.e., the agents are urea, thioruea, selenourea, and tellurourea respectively. The preferred complex-forming agents are urea and thiourea, with the most preferred agent being urea.

The specific liquid organofunctional polysiloxanes of this invention which have been found to unexpectedly form inclusion adducts with the complex-forming agents above are of the general formula:

V 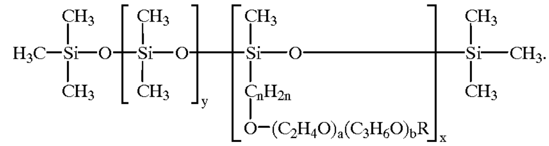 wherein n is from 2 to 6, preferably 3; a is from 6 to 25; preferably 8 to 15, more typically about 8 to about 11, and b is from 0 to 25; preferably from 0 to 15, it being understood that the oxyalkylene groups may be random and/or block mixtures of oxyalkylene units; y is in the range of from 0 to 5, preferably zero; x is in the range of from 1 to 5; preferably 1, and in which R can be hydrogen; an alkyl group having 1 to 4 carbon atoms; or an alkyl ester group wherein the alkyl group of the ester has from 1 to 4 carbon atoms.

The silicone glycols described above are known in the art and may be prepared by coupling the corresponding alkyl-terminated glycol to a bis-siloxane structure having a hydrogen attached to the central silicon atom, said structure being

VI

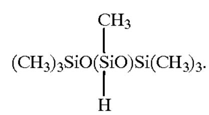

Generally, the coupling is accomplished in the presence of a platinum catalyst. In such coupling reactions, a fraction of the alkyl-terminated glycol is not converted and will remain as an impurity in the final silicone glycol product.

Silicone glycol-silicone alkane terpolymers also may be used to form the inclusions complexes of the instant invention. These compounds may be represented by the average formula:

VII 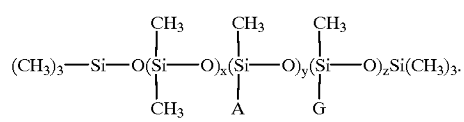 wherein A is a linear or branched alkyl radical having 6 to 30 carbon atoms, G is a glycol moiety having the formula $-R'O\ CH_2CH_2)_mOR''$ in which R' is a divalent alkylene group having 2 to 6 carbon atoms, R" is selected from the group consisting of hydrogen; an alkyl radical having 1 to 4 carbon atoms; an alkyl ester group wherein the alkyl group of the ester has from 1 to 4 carbon atoms; m is 8 to 100; x is 0 to 5, preferably 0; y is 0.1 to 2.5, preferably 0.1 to 1.25; and z is 0.1 to 5.0, preferably 0.75 to 1.9.

The preparation of these silicone glycol-silicone alkane terpolymers which is described in U.S. Pat. No. 5,059,704 (incorporated herein) is well known in the art.

In order to obtain a non-tacky, i.e., dry free-flowing inclusion complex with the ethoxylated polysiloxanes of this invention alone, it has been observed that when the ethoxy chain length is less than about 12 units in length, the maximum weight percent of the surfactant in the complex decreases rapidly from about 50 wt. % at that chain length to about 12 weight percent when the ethoxy chains are about 8 units in length. Again, this observation was made in the context of the only material mixed with the urea during the complexing process is the organosilicone surfactant. Thus, an organosilicone surfactant having an ethoxy chain length of less than about 12 units in length will typically be non-clathratable.

As used herein, the term "polyoxyethylene" denotes simply a compound which contains more than one oxyethylene unit. Examples of particularly useful readily clathratable polyoxyethylenes are ethoxylated fatty alcohols, ethoxylated fatty acids, or ethoxylated alkylphenols having at least 8 oxyethylene units per alcohol or acid group, typically from about 9 to about 24 oxyethylene units per alcohol or acid group. The ethoxylated fatty alcohols and fatty acids typically have predominantly (on a weight basis) from about 8 to about 24 carbon atoms in the fatty chain, more typically from about 12 to about 18 carbon atoms in the fatty chain, and may be straight chain or branched chain. The ethoxylated alkyl phenols typically have predominantly (on a weight basis) one or more alkyl groups of from about 4 to about 12, more typically from about 8 to about 10 carbon atoms. Specific examples of ethoxylated fatty alcohols are the branched chain isotridecyl alcohol ethoxylates having 9–10 and 15 oxyethylene units, available from Rhône-Poulenc, Inc. as RHODASURF BC-720 and BC-840, respectively, and mixed linear alcohol ethoxylates having 12 to 25 oxyethylene units, available from Rhône-Poulenc, Inc. as RHODASURF LA-12 and LA-25, respectively. Specific examples of ethoxylated alkylphenols are the nonylphenol ethoxylates having 12 and 30 oxyethylene units, available from Rhône-Poulenc, Inc. as IGEPAL CO-720 and CO-880, respectively. Further examples of useful readily clathratable polyoxyethylenes include polyoxyethylene homopolymers (optionally started with a lower alkanol (e.g. $C_1$–$C_4$), e.g. a butyl carbinol) having at least about 8 oxyethylene units and block copolymers of ethylene oxide and propylene oxide, provided the block copolymer has at least about 8 oxyethylene units and a molar ratio of oxyethylene units to oxypropylene units of greater than about 0.87:1, more typically greater than about 9.90:1, more typically greater than about 1.0:1, and even more typically at least about 1.04:1. Typically, the ratio of oxyethylene units to oxypropylene units will be less than about 2:1, more typically less than about 1.5:1, and most typically at most about 1.35:1. Specific examples of polyoxyethylene homopolymers include homopolymers having molecular weights (e.g. weight average) of 400, 600 and 1000, (i.e. having about 9, 18 and 23 repeating oxyethylene units, respectively) available from Rhône-Poulenc, Inc. as RHODASURF E-400, E-600 and E-1,000, respectively, and specific examples of block copolymers of ethylene oxide and propylene oxide include ethylene oxide capped polypropylene glycols having 44 oxyethylene and 39 oxypropylene units, 150 oxyethylene and 30 oxypropylene units, 194 oxyethylene and 39 oxypropylene units; 22 oxyethylene and 21 oxypropylene units, and 22 oxyethylene and 16 oxypropylene units available from Rhône-Poulenc, Inc. as ANTAROX P-84, F-68, F-88, L-44 and L-35 respectively.

The non-clathratable polyoxyethylenes are typically polyoxyethylene homopolymers (optionally started with an alkanol, typically a lower (i.e. $C_1$–$C_4$) alkanol, e.g. a butyl carbinol) having less than about 8 oxyethylene units and block copolymers of ethylene oxide and propylene oxide, provided the block copolymer has less than about 8 oxyethylene units or a molar ratio of oxyethylene units to oxypropylene units of at most about 1.04:1, typically at most about 1.0:1, more typically at most about 0.90:1, and even more typically at most about 0.87:1. Typically, the ratio of oxyethylene units to oxypropylene units will be greater than about 0.1:, more typically greater than about 0.25:1, and most typically at least about 0.45:1. Specific examples of non-clathratable polyoxyethylenes include ethylene oxide capped polypropylene glycols having 26 oxyethylene and 30 oxypropylene units, 16 oxyethylene and 35 oxypropylene units, and 14 oxyethylene and 21 oxypropylene units; available from Rhône-Poulenc, Inc. as ANTAROX L-72, L-64 and L-43 respectively. Further examples include ethoxylated fatty alcohols, ethoxylated fatty acids, or ethoxylated alkylphenols having less than about 8 oxyethylene units per alcohol or acid group, typically from about 4 to about 7 oxyethylene units per alcohol or acid group. The ethoxylated fatty alcohols and fatty acids typically have predominantly (on a weight basis) from about 8 to about 24 carbon atoms in the fatty chain, more typically from about 12 to about 18 carbon atoms in the fatty chain, and may be straight chain or branched chain. The ethoxylated alkyl phenols typically have predominantly (on a weight basis) one or more alkyl groups of from about 4 to about 12, more typically from about 8 to about 10 carbon atoms. Specific examples of ethoxylated fatty alcohols are the branched chain isotridecyl alcohol ethoxylates having 5, 6, and 7 oxyethylene units, available from Rhône-Poulenc, Inc. as RHODASURF BC-520, BC-610, and BC-630, respectively.

It is necessary that the components of the complex of this invention be at least partially soluble in or miscible with water. Nonionic surfactants such as hydroxy ethoxylated alkylphenols have been prepared in molten urea, with or without the presence of organic solvent. However, for the preferred agricultural end uses of this invention, the melt processes are undesirable because of the possible formation of the biuret. Under melt conditions, the urea can degrade to imido-dicarbonic-diamide (a.k.a. carbamyl urea: $NH_2CONHCONH_2$) a phytotoxic compound.

Although there are a variety of other methods by which complexation may be realized, e.g., freeze drying and prilling, the preferred method is as follows:

i) the water miscible ethoxylated polysiloxane is added and intimately mixed with an aqueous solution, preferably a saturated aqueous solution of a complexing agent, preferably urea at from about 50° to about 80° C.;

ii) the temperature of the polysiloxane-complexing agent solution is lowered to below the dissociation temperature of the newly formed complex; usually to below about 50° C.;

iii) the water is evaporated until a thick, non-flowing paste is formed;

iv) the paste is further dried until the water content is below about 10 weight percent by Karl Fischer titration, preferably by preparing a spread on a tray to a depth of about ¼ inch and placing the paste and tray in an oven at about 50° C.; and v) the dried, flaked complex is ground to a fine powder.

If the product of the above procedure is a single-phase solid by macroscopic observation (i.e. to the naked eye), then the product may be a clathrate. The presence of an inclusion complex is confirmed via use of a Differential Scanning Calorimeter (DSC) (TA Instruments Model 910 DSC). Samples are placed in a hermetic pan with a pinhole lid and inserted into the DSC with an air flow of about 50 ml./min. The DSC is generally operated at from −50° C. to 300° C. with a temperature change rate of 10° C./min. The presence of a clathrate is indicated by the appearance of a DSC thermal transition or peak for the dissociation of the clathrate. A material is considered readily clathratable if a dry solid results from the use of the material at a 1:1 weight ratio of material to urea in the above standard clathration process, provided the dry solid shows essentially complete (e.g. a greater than 95% conversion) conversion of the material to clathrate. Conversion is detected by a reduction of at least 95% of the DSC peak for the material in the DSC of the product of the standard clathration test, the reduction being measured by comparison to a 1:1 blend of the material and urea that has not been subjected to the standard clathration process (e.g. obtained by simple mixing of the material and urea).

Whereas the exact scope of the instant invention is set forth in the appended claims, the following specific examples illustrate certain aspects of the present invention and, more particularly, point out methods of evaluating same. The examples are set forth for illustration only and are not to be construed as limitations on the present invention. All parts, ratios, and percentages in this specification and the appended claims are by weight unless otherwise indicated.

EXAMPLES

Comparative Examples A–D

An aqueous solution of urea is prepared and heated to 70° C. While maintaining this temperature, a sufficient amount of an ethoxylated trisiloxane surfactant of the average formula:

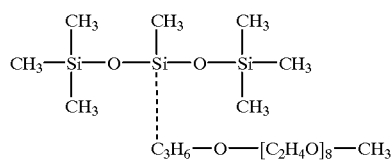

VIII sold under the trademark SILWET L-77® by OSI Specialties, Inc. is added such that the weight ratio of surfactant to urea is 12:88. Once the surfactant and urea are in solution, the temperature is lowered to about 50° C. The solution is maintained at that temperature until sufficient water has evaporated so that a thick, non-flowing paste is formed. The paste is then spread on a tray to a depth of about ¼ inch and the tray placed in an oven at 50° C. until the water content of the inclusion complex thus formed is less than about 1 weight percent, as determined by Karl Fischer titration.

Additional samples are prepared in a like manner wherein the weight ratio of surfactant to urea is 10:90; 15:85; and 31:69.

The oven dried 10 and 12 weight percent material is subsequently ground to a fine, dry free-flowing powder. The oven dried 14 weight percent material, although able to be ground, remains very slight tack. The oven dried 31 weight percent material remains very tacky.

DSC analysis confirms that with the 10 weight percent and 12 weight percent essentially no free polysiloxane is present and that all detectable polysiloxane has associated with the urea, by inference as inclusion complex.

Figure 2:
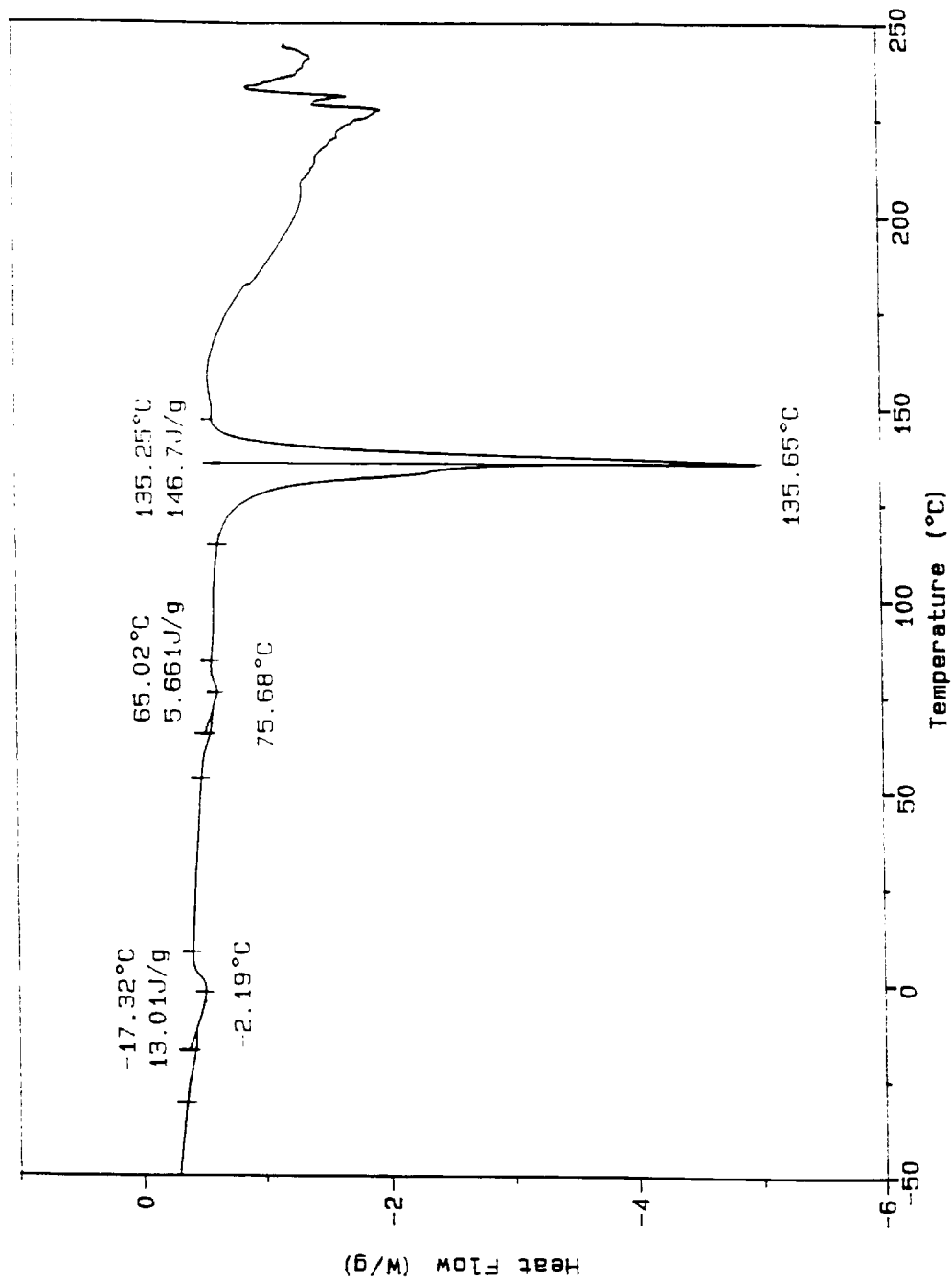
FIG. 2 is a graphic depiction of the data generated by a DSC scan of 31 weight percent of SILWET L-77® ethoxylated polysiloxane after clathration has been attempted as set forth in Comparative Examples A–D.
Figure 3:
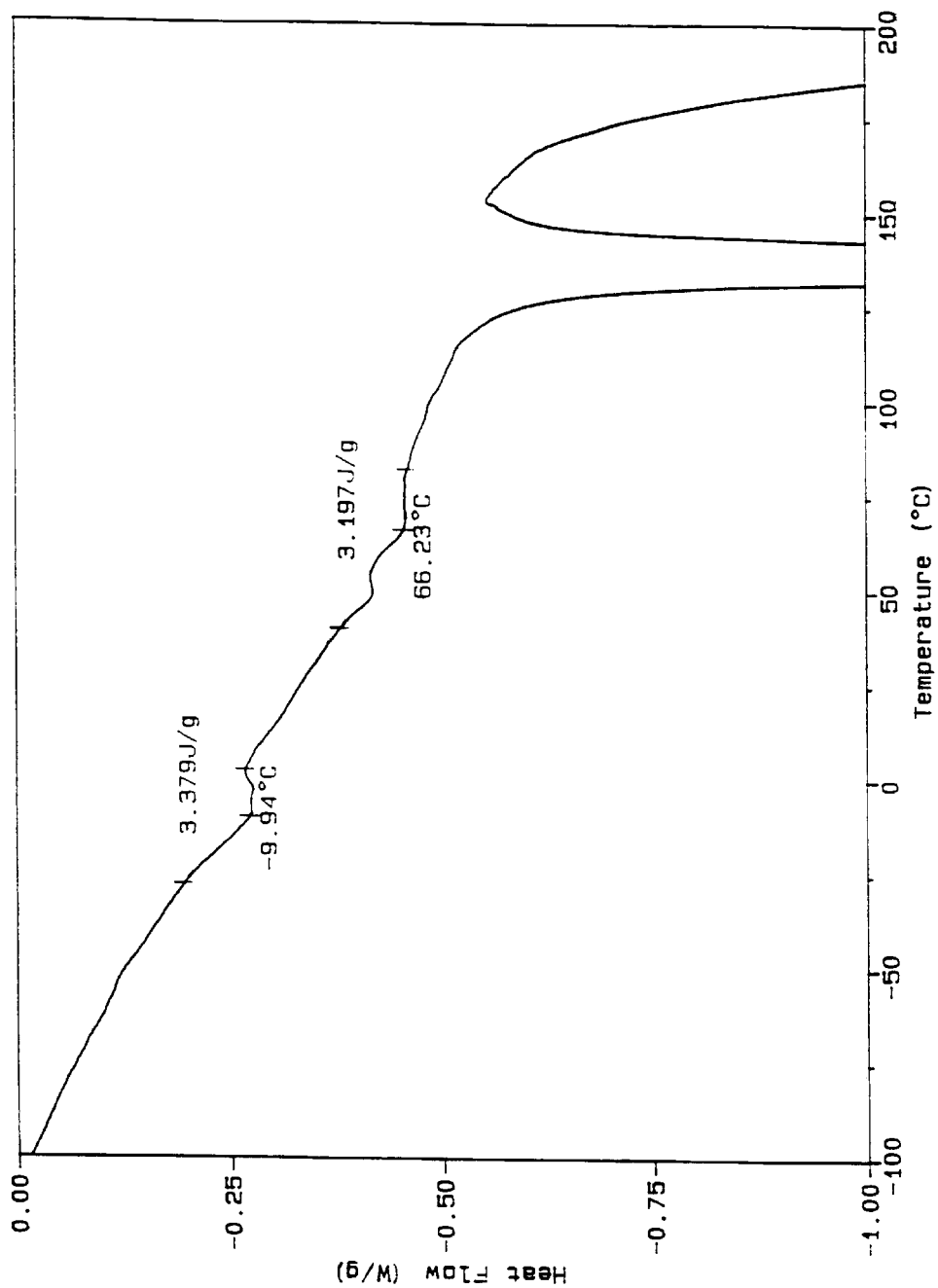
FIG. 3 is a graphic depiction of the data generated by a DSC scan of 10 weight percent SILWET L-77® ethoxylated polysiloxane after clathration has been attempted as set forth in Comparative Examples A–D.

FIG. 1 is illustrative of a DSC scan of SILWET L-77® ethoxylated polysiloxane alone. FIG. 2 is illustrative of the DSC scanning results realized on the product obtained via the urea processing of Examples I–IV at a 31 weight percent polysiloxane loading. Note the SILWET L-77® peak at −17.32° C. FIG. 3 is a graphic depiction of the data generated by a DSC scan of 10 weight percent SILWET L-77® ethoxylated polysiloxane after clathration has been attempted as set forth in Example I.

Comparative Example E

An aqueous solution of urea is prepared and heated to 70° C. While maintaining this temperature, a sufficient amount of the liquid ethoxylated trisiloxane surfactant of the average formula:

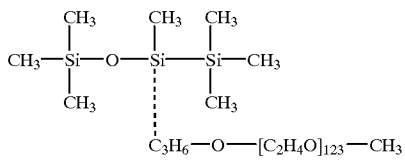

is added to the urea such that the weight ratio of surfactant to urea in each solution is 50:50.

Once the surfactant and urea are in solution, the temperature of the solution is lowered to about 50° C. and the procedures in Examples A–D followed until the material has a water content below 1 weight percent.

The resulting solid forms, when ground, a fine white dry free-flowing powder.

50 grams of the dry inclusion complex powder formed from this polysiloxane was added to 1 liter of water at room temperature with moderate stirring. The complex dissolved rapidly to a clear solution.

Comparative Examples F–K

The procedures of Comparative Examples A–D are followed with the surfactant compounds identified in Table I below in lieu of the polysiloxane surfactant. In all cases, the weight ratio of the surfactant to urea is 10:90.

TABLE I

| | |
|---|---|
| F. | $\underset{\text{HO(CH}_2\text{CH}_2\text{O)}_{13}\text{(CH}_2\text{CHO)}_{30}\text{(CH}_2\text{CH}_2\text{O)}_{13}\text{H}}{\overset{\mid}{\text{CH}_3}}$ *1 |
| G. | $\underset{\text{HO(CH}_2\text{CH}_2\text{O)}_8\text{(CH}_2\text{CHO)}_{35}\text{(CH}_2\text{CH}_2\text{O)}_8\text{H}}{\overset{\mid}{\text{CH}_3}}$ *2 |
| H. | $\underset{\text{HO(CH}_2\text{CH}_2\text{O)}_7\text{(CH}_2\text{CHO)}_{21}\text{(CH}_2\text{CH}_2\text{O)}_7\text{H}}{\overset{\mid}{\text{CH}_3}}$ *3 |
| I. | Isotridecyl Alcohol Ethoxylate [5 EO]*4 |
| J. | IsofridecylAlcohol Ethoxylate [6 EO]*5 |
| K. | Isotridecyl Alcohol Bthoxylate [7 EO]*6 |

1 ANTAROX L64; a trademark of Rhone-Poulenc Inc.

2 ANTAROX L72; a trademark of Rhone-Poulenc Inc.

3 ANTAROX L43, a trademark of Rhône-Poulenc Inc.

4 RHODASURF BC-520 Alcohol Ethoxylate, a trademark of Rhone-Poulenc Inc.

5 RHODASURF BC-610 Alcohol Ethoxylate, a trademark of Rhone-Poulenc Inc.

6 RHODASURF BC-630 Alcohol Ethoxylate, a trademark of Rhone-Poulenc Inc.

None of the above ethoxylated surfactants form a molecular inclusion complex with urea and show no conversion to clathrate or, if any conversion was detected, at least a 95% reduction.

Comparative Examples L–Y

The procedures of Comparative Examples A–D are followed with the surfactant compounds identified in Table II below in lieu of the polysiloxane surfactant used in Comparative Examples A–D. In all cases, the weight ratio of the surfactant to urea is 50:50.

TABLE II

| | |
|---|---|
| L. | Isotridecyl Alcohol Ethoxylate [9–10 EO][*7] |
| M. | Isotridecyl Alcohol Ethoxylate [15 EO][*8] |
| N. | Mixed Linear Alcohol Ethoxylate [12 EO][*9] |
| O. | Mixed Linear Alcohol Ethoxylate [25 EO][*10] |
| P. | Nonylphenol Ethoxylate [12 EO][*11] |
| Q. | Nonylphenol Ethoxylate [25 EO][*12] |
| R. | $HO(CH_2CH_2O)_9H$[*13] |
| S. | $HO(CH_2CH_2O)_{18}H$[*14] |
| T. | $HO(CH_2CH_2O)_{23}H$[*15] |
| U. | $HO(CH_2CH_2O)_{22}(CH_2\overset{\underset{\mid}{CH_3}}{C}HO)_{39}(CH_2CH_2O)_{22}H$[*16] |
| V. | $HO(CH_2CH_2O)_{75}(CH_2\overset{\underset{\mid}{CH_3}}{C}HO)_{30}(CH_2CH_2O)_{75}H$[*17] |
| W. | $HO(CH_2CH_2O)_{97}(CH_2\overset{\underset{\mid}{CH_3}}{C}HO)_{39}(CH_2CH_2O)_{97}H$[*18] |
| X. | $HO(CH_2CH_2O)_{11}(CH_2\overset{\underset{\mid}{CH_3}}{C}HO)_{21}(CH_2CH_2O)_{11}H$[*19] |
| Y. | $HO(CH_2CH_2O)_{11}(CH_2\overset{\underset{\mid}{CH_3}}{C}HO)_{16}(CH_2CH_2O)_{11}H$[*20] |

7 RHODASURF BC-720; a trademark of Rhone-Poulenc Inc.

8 RHODASURF BC-840; a trademark of Rhone-Poulenc Inc.

9 RHODASURF LA-12, a trademark of Rhône-Poulenc Inc.

10 RHODASURF LA-25; a trademark of Rhone-Poulenc Inc.

11 IGEPAL CO-720; a trademark of Rhone-Poulenc Inc.

12 IGEPAL CO-880, a trademark of Rhone-Poulenc Inc.

13 RHODASURF E-400; a trademark of Rhone-Poulenc Inc.

14 RHODASURF E-600; a trademark of Rhone-Poulenc Inc.

15 RHODASURF E-1000; a trademark of Rhone-Poulenc Inc.

16 ANTAROX P-84 a trademark of Rhône-Poulenc Inc.

17 ANTAROX F-68, a trademark of Rhône-Poulenc Inc.

18 ANTAROX F-88, a trademark of Rhône-Poulenc Inc.

19 ANTAROX L-44, a trademark of Rhône-Poulenc Inc.

20 ANTAROX L-35, a trademark of Rhône-Poulenc Inc.

Figure 5:
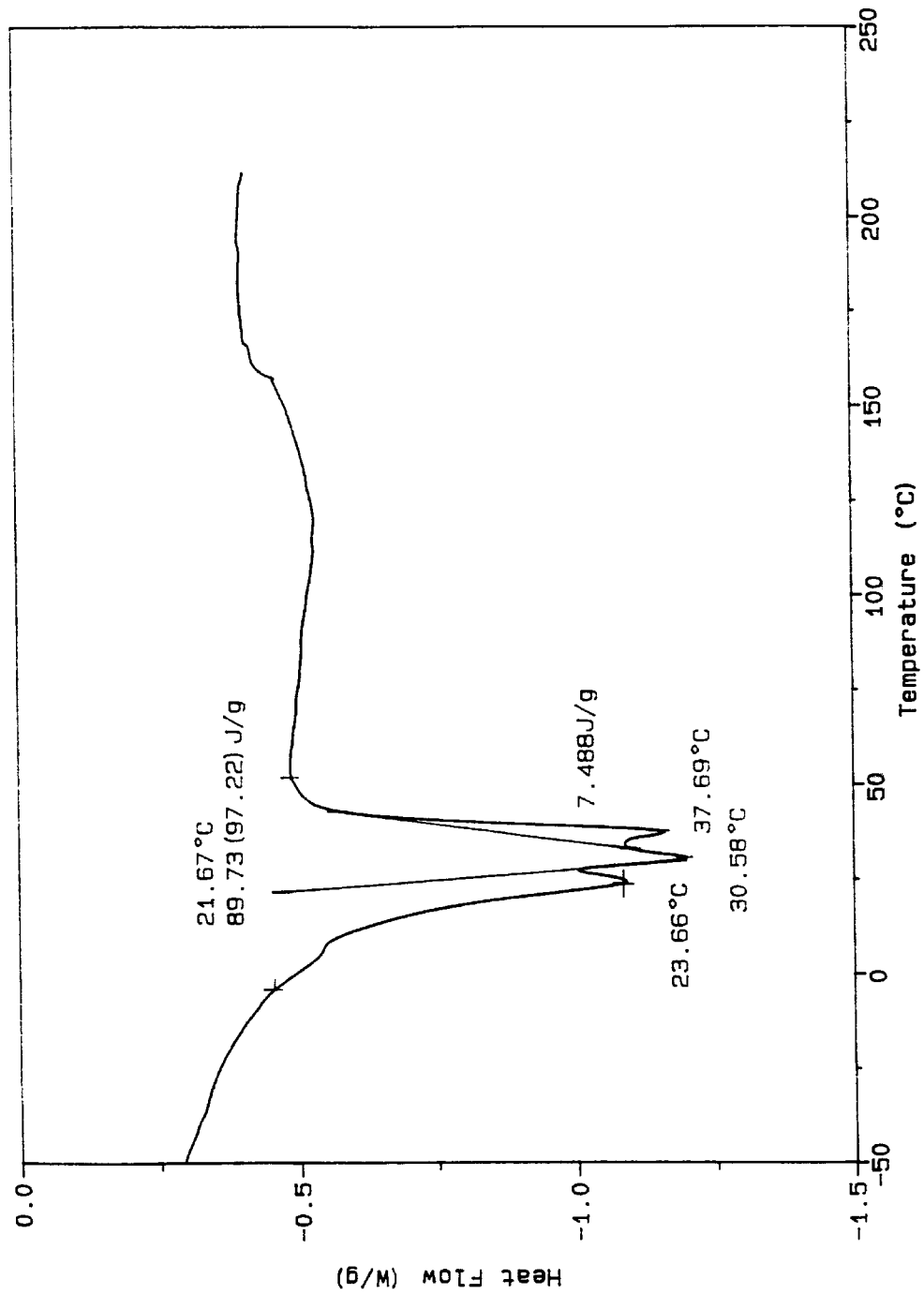
FIG. 5 is a graphic depiction of the results of a DSC scan of unclathrated RHODASURF BC-840 alcohol ethoxylate.
Figure 6:
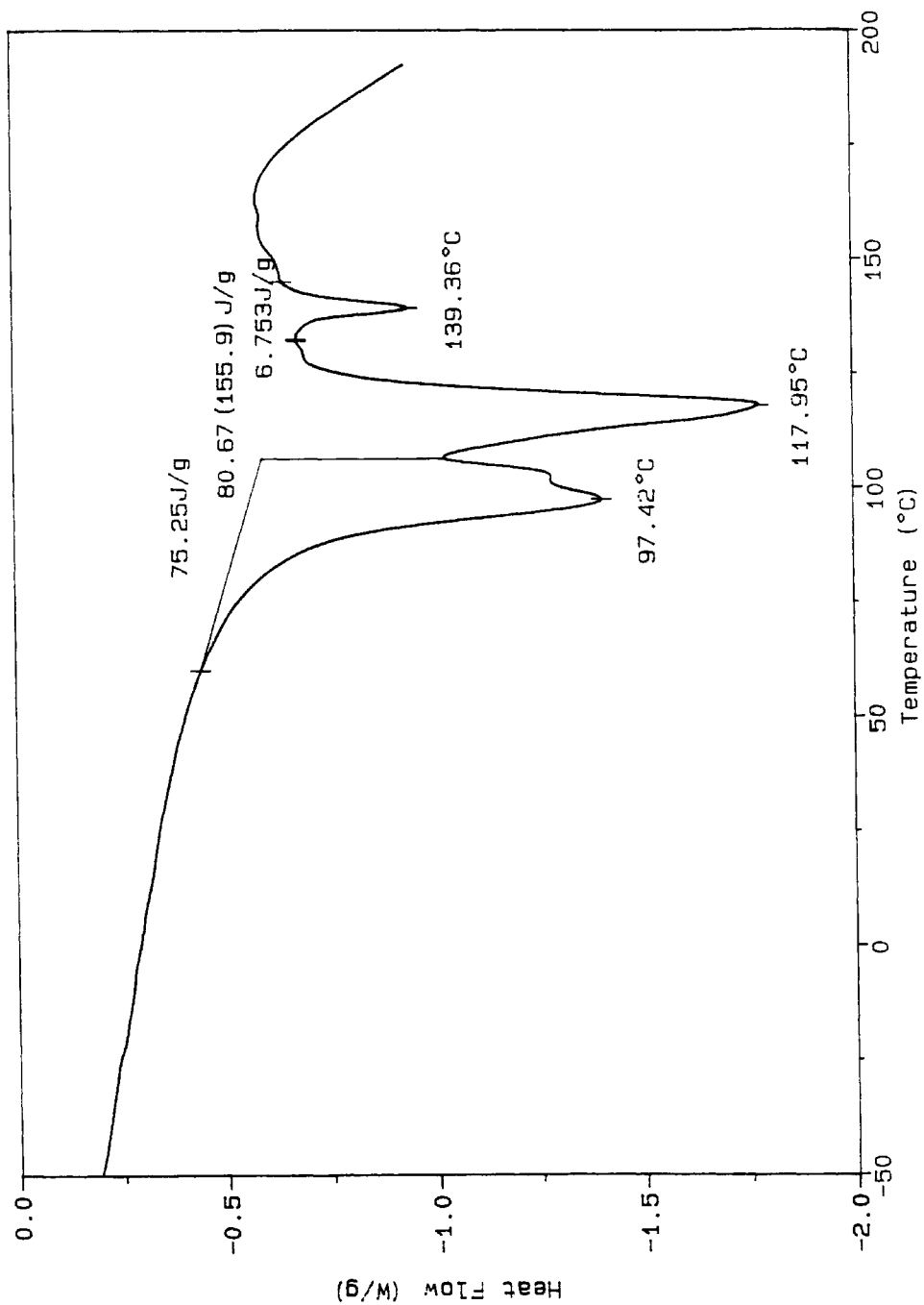
FIG. 6 is a graphic depiction of the results of a DSC scan of RHODASURF BC-840 alcohol ethoxylate after clathration has been attempted as set forth in Comparative Example M.

All of the above polyethoxylates form a molecular inclusion complex with urea as a dry, solid, free-flowing single-phase material and showed at least a 95% conversion to clathrate. For example, compare the DSC scan shown in FIG. 6, which is a scan of the product of Comparative Example M, with the DSC scan shown in FIG. 5, which is RHODASURF BC-840 alone.

EXAMPLES 1–8

The procedures of Comparative Examples A–D are followed with the compounds identified in Table III below and the polysiloxane surfactant of Comparative Examples A–D (i.e. Silwet L-77). In all cases, the weight ratio of the compound to polysiloxane surfactant to urea is 25:25:50.

TABLE III

| | |
|---|---|
| 1. | Isotridecyl Alcohol Ethoxylate [15 EO][*21] |
| 2. | Nonylphenol Ethoxylate [12 EO][*22] |
| 3. | $HO(CH_2CH_2O)_9H$[*23] |
| 4. | $HO(CH_2CH_2O)_{13}H$[*24] |
| 5. | $HO(CH_2CH_2O)_{23}H$[*25] |
| 6. | $HO(CH_2CH_2O)_{22}(CH_2\overset{\underset{\mid}{CH_3}}{C}HO)_{39}(CH_2CH_2O)_{22}H$[*26] |
| 7. | $HO(CH_2CH_2O)_{75}(CH_2\overset{\underset{\mid}{CH_3}}{C}HO)_{30}(CH_2CH_2O)_{75}H$[*27] |
| 8. | $HO(CH_2CH_2O)_{97}(CH_2\overset{\underset{\mid}{CH_3}}{C}HO)_{39}(CH_2CH_2O)_{97}H$[*28] |

21 RHODASURF BC-840; a trademark of Rhone-Poulenc Inc.

22 IGEPAL CO-720; a trademark of Rhone-Poulenc Inc.

23 RHODASURF E-400; a trademark of Rhone-Poulenc Inc.

24 RHODASURF E-600; a trademark of Rhone-Poulenc Inc.

25 RHODASURF E-1000; a trademark of Rhone-Poulenc Inc.

26 ANTAROX P-84 a trademark of Rhône-Poulenc Inc.

27 ANTAROX F-68, a trademark of Rhône-Poulenc Inc.

Figure 7:
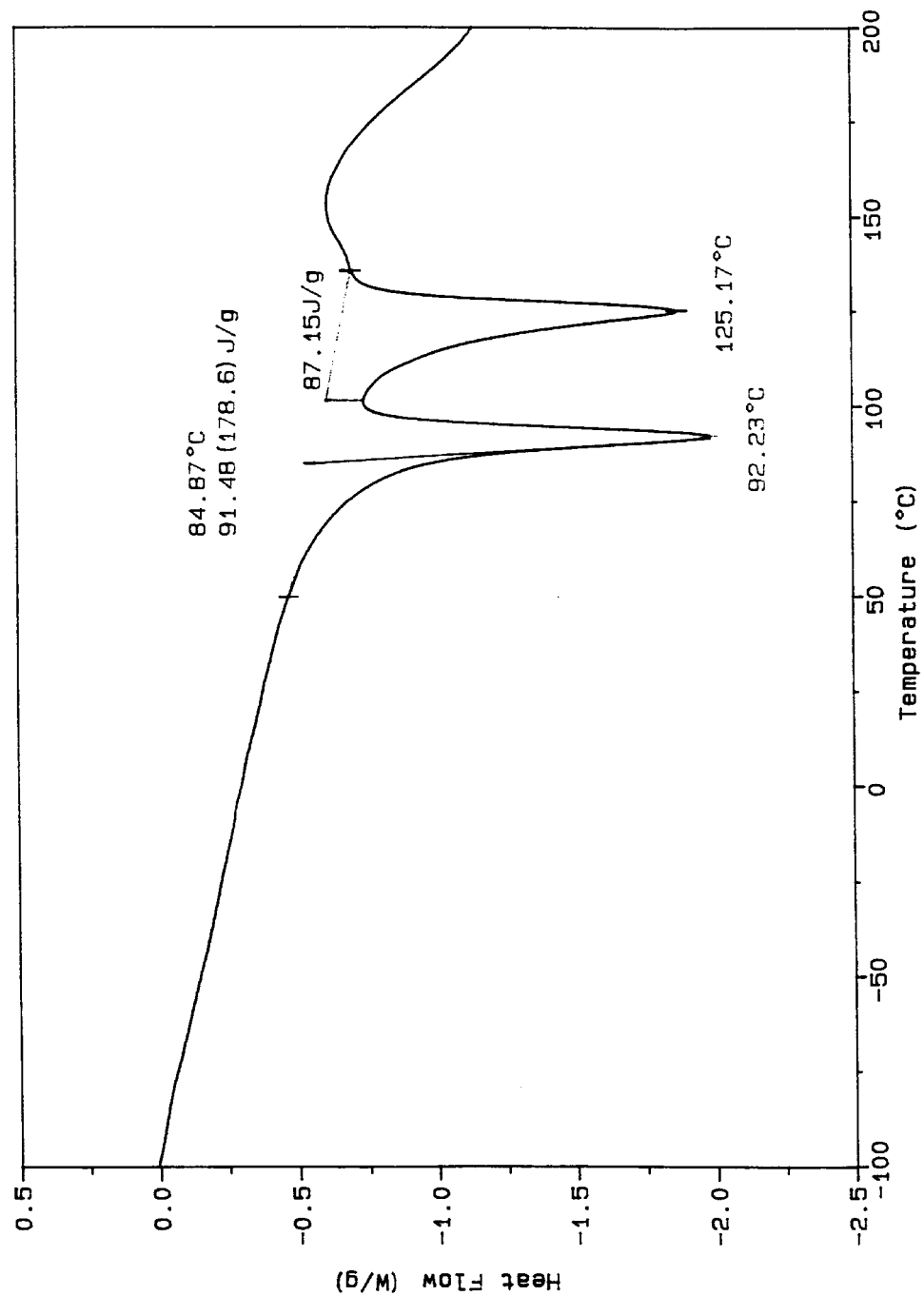
FIG. 7 is a graphic depiction of the results of a DSC scan of RHODASURF BC-840 alcohol ethoxylate and SILWET L-77® polysiloxane after clathration has been attempted as set forth in Example 1.

All of the above compounds with the polysiloxane surfactant formed a molecular inclusion complex with urea as a dry, solid, free-flowing single-phase material which exhibited no detectable DSC thermal transition for any of the individual components except urea. For example, compare the DSC scan shown in FIG. 7, with is a scan of the product of Example 1, with the DSC scans shown in FIG. 5, with is RHODASURF BC-840 alone and in FIG. 1, which is SILWET L-77 alone.

EXAMPLE 9

Figure 4:
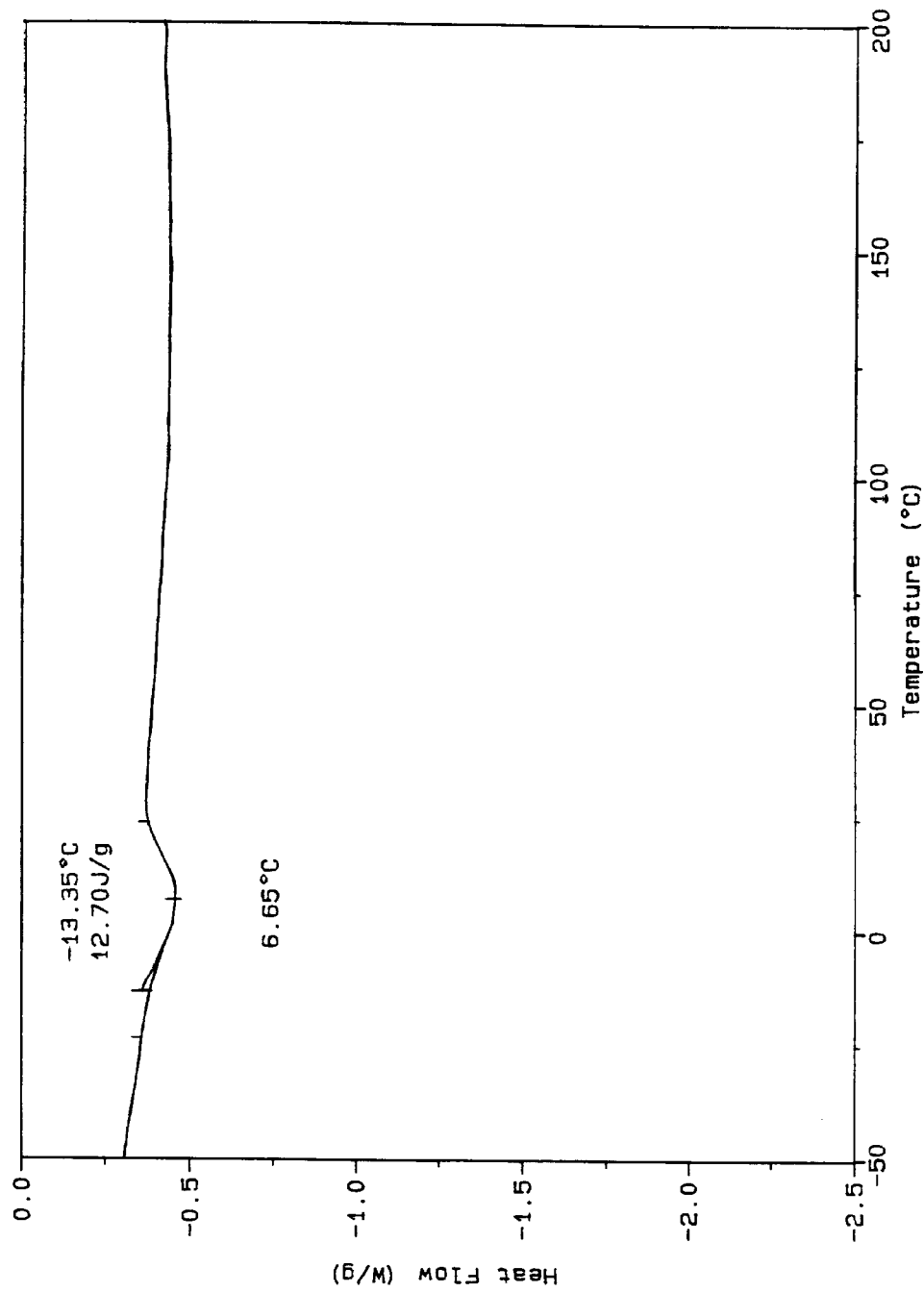
FIG. 4 is a graphic depiction of the results of a DSC scan of unclathrated ANTAROX L-72 block copolymer of ethylene and propylene oxides.
Figure 8:
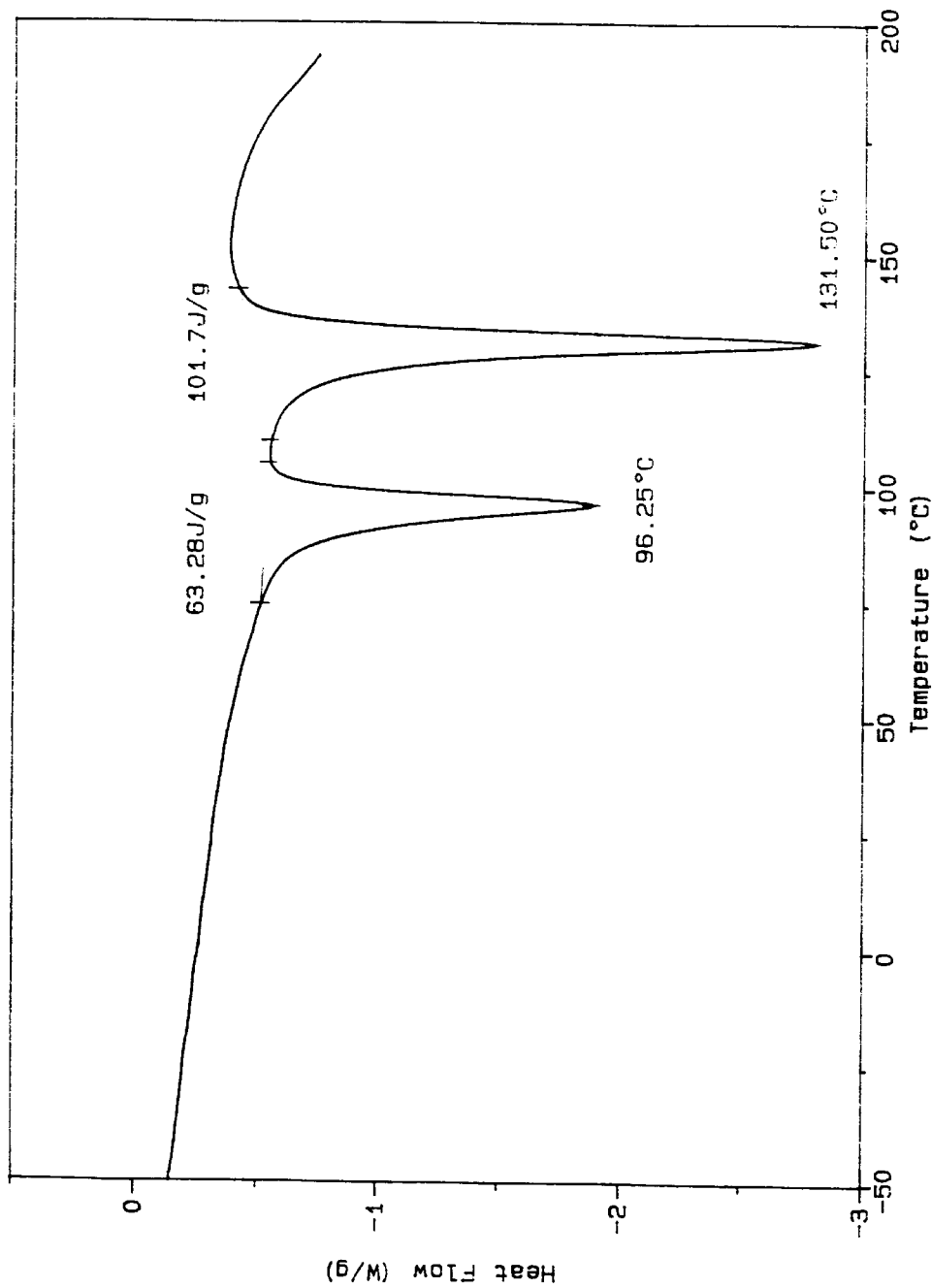
FIG. 8 is a graphic depiction of the results of a DSC scan of RHODASURF BC-840 alcohol ethoxylate, SILWET L-77® polysiloxane, and ANTAROX L-72 block copolymer of ethylene and propylene oxides after clathration has been attempted as set forth in Example 9.

The procedure of Comparative Examples A–D is followed with the isotridecyl alcohol ethoxylate [15 EO] of Comparative Example M, (i.e. RHODASURF BC-840), the polysiloxane surfactant of Comparative Examples A–D (i.e. SILWET L-77), and the block copolymer of ethylene oxide and propylene oxide having (8 EO/35 PO/8 EO) of comparative Example G (i.e. ANTAROX L-72). The weight ratio of the isotridecyl ethoxylate to polysiloxane surfactant to block copolymer to urea is 25:12.5:12.5:50. The resulting product was a dry, solid, free-flowing, single-phase molecular inclusion complex which exhibited no detectable DSC thermal transition for any of the individual components, except urea. Compare the DSC scan shown in FIG. 8, which is a scan of the product of Example 9, with the DSC scans shown in FIG. 5, which is RHODASURF BC-840 alone, in FIG. 1, which is SILWET L-77 alone, and in FIG. 4, which is ANTAROX L-72 alone.

What is claimed is:

1. A composition comprising a solid, water-soluble complex comprising:

a) a polysiloxane of the formula:

$$H_3C-Si(CH_3)_2-O-[Si(CH_3)_2-O]_y-[Si(CH_3)(C_nH_{2n}O-(C_2H_4O)_a(C_3H_6O)_bR)-O]_x-Si(CH_3)_2-CH_3$$

wherein n is from about 2 to about 6; a is from about 8 to about 25; and b is from 0 to about 25; and the oxyalkylene groups may be random or block mixtures; y is from 0 to about 5; x is from about 1 to about 5; and R is selected from the group consisting of hydrogen, $C_1$–$C_4$ alkyl, and a $C_1$–$C_4$ alkyl ester; or $$H_3C-Si(CH_3)_2-O-[Si(CH_3)_2-O]_y-[Si(CH_3)(A)-O]_x-[Si(CH_3)(G)-O]_z-Si(CH_3)_2-CH_3$$

wherein A is a linear or branched alkyl having about 6 to about 30 carbon atoms; G is a glycol moiety of the formula —R' (OCH$_2$CH$_2$)$_m$OR" wherein R' is a divalent alkylene group having about 2 to about 6 carbon atoms; R" is selected from the group consisting of hydrogen, $C_1$–$C_4$ alkyl, and a $C_1$–$C_4$ alkyl ester; m is about 8 to about 100; y is 0 to about 5; X is about 0.1 to about 2.5; and z is about 0.1 to about 5.0;

b) a complex-forming agent of the formula:

$$H_2N-C(=X)-NH_2$$

wherein X is O, S, Se, or Te, and c) a readily clathratable polyoxyethylene selected from the group of ethoxylated fatty alcohols, ethoxylated fatty acids, and ethoxylated alkylphenols, each having at least 8 oxyethylene units per alcohol or acid group and polyoxyethylene homopolymers, optionally started with a lower alkanol, having at least about 8 oxyethylene units and block copolymers of ethylene oxide and propylene oxide, provided the block copolymer has at least about 8 oxyethylene units and a molar ratio of oxyethylene units to oxypropylene units of greater than about 0.87:1.

2. The composition of claim 1 wherein said readily clathratable polyoxyethylene has from about 9 to about 24 oxyethylene units per alcohol or acid group.

3. The composition of claim 1 wherein said readily clathratable polyoxyethylene is an ethoxylated fatty alcohol or fatty acid having predominantly on a weight basis of from about 8 to about 24 carbon atoms in the fatty chain.

4. The composition of claim 1 wherein said readily clathratable polyoxyethylene is an ethoxylated fatty alcohol or fatty acid having predominantly on a weight basis of from about 12 to about 18 carbon atoms in the fatty chain.

5. A composition comprising a solid, water-soluble complex comprising:

a) a polysiloxane of the formula:

$$H_3C-Si(CH_3)_2-O-[Si(CH_3)_2-O]_y-[Si(CH_3)(C_nH_{2n}O-(C_2H_4O)_a(C_3H_6O)_bR)-O]_x-Si(CH_3)_2-CH_3$$

wherein n is from about 2 to about 6; a is from about 8 to about 25; and b is from 0 to about 25; and the oxyalkylene groups may be random or block mixtures; y is from 0 to about 5; x is from 1 to about 5; and R is selected from the group consisting of hydrogen, $C_1$–$C_4$ alkyl, and a $C_1$–$C_4$ alkyl ester;

b) urea, and c) a readily clathratable polyoxyethylene selected from the group of ethoxylated fatty alcohols, ethoxylated fatty acids, and ethoxylated alkylphenols, each having at least 8 oxyethylene units per alcohol or acid group and polyoxyethylene homopolymers, optionally started with a lower alkanol, having at least about 8 oxyethylene units and block copolymers of ethylene oxide and propylene oxide, provided the block copolymer has at least about 8 oxyethylene units and a molar ratio of oxyethylene units to oxypropylene units of greater than about 0.87:1.

6. The composition of claim 5 wherein the polysiloxane is of the formula:

$$H_3C-Si(CH_3)_2-O-Si(CH_3)(C_nH_{2n}O-(C_2H_4O)_a(C_3H_6O)_bR)-O-Si(CH_3)_2-CH_3$$

wherein n is 3; a is about 8 to about 15; and b is 0.

7. The composition of claim 6 wherein the polysiloxane is present up to 40 weight percent based on the total weight of the complex.

8. The composition of claim 6 wherein R is —CH$_3$ and a is about 8.

9. The composition of claim 5 wherein the polysiloxane is present up to 40 weight percent based on the total weight of the complex.

10. The composition of claim 9 wherein y is 0, x is about one, R is —CH$_3$ and a is about 8.

11. The composition of claim 5 wherein the weight ratio of said readily clathratable polyoxyethylene to said polysiloxane is from about 166:1 to about 1:3.

12. The composition of claim 5 wherein the weight ratio of said readily clathratable polyoxyethylene to said polysiloxane is from about 2:1 to about 1:2.

13. The composition of claim 5 wherein the weight ratio of the sum of the weights of the readily clathratable polyoxyethylene and the polysiloxane to urea is from about 3:2 to about 1:19.

14. The composition of claim 5 wherein said readily clathratable polyoxyethylene is an ethoxylated fatty alcohol having predominantly on a weight basis of from about 12 to about 18 carbon atoms in the fatty chain and from about 8 to about 23 oxyethylene units.

15. A composition comprising a solid, water-soluble complex comprising:

a) a polysiloxane of the formula:

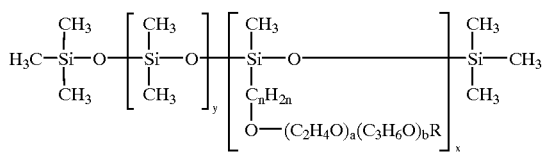

wherein n is from about 2 to about 6; a is from about 8 to about 11; and b is from 0 to about 25; and the oxyalkylene groups may be random or block mixtures; y is from 0 to about 5; x is from about 1 to about 5; and R is selected from the group consisting of hydrogen, $C_1$–$C_4$ alkyl, and a $C_1$–$C_4$ alkyl ester;
  b) a readily clathratable polyoxyethylene selected from the group ethoxylated fatty alcohols, ethoxylated fatty acids, and ethoxylated alkylphenols, each having at least 8 oxyethylene units per alcohol or acid group and polyoxyethylene homopolymers, optionally started with a lower alkanol, having at least about 8 oxyethylene units and block copolymers of ethylene oxide and propylene oxide, provided the block copolymer has at least about 8 oxyethylene units and a molar ratio of oxyethylene units to oxypropylene units of greater than about 1.04:1, wherein the weight ratio of readily clathratable polyoxyethylene to polysiloxane is from about 1.5:1 to about 1:1.5, and
  c) urea, wherein the weight ratio of the sum of the weights of the readily clathratable polyoxyethylene and polysiloxane to urea is from about 0.95:1 to 1.05:1.

16. The composition of claim 15, wherein "a" is from about 8 to about 10.

17. The composition of claim 16, wherein n is 3, b is zero, y is 1, x is 1, and R is methyl.

18. The composition of claim 17 wherein "a" is 8.

19. The composition of claim 18 wherein said readily clathratable polyoxyethylene is an ethoxylated tridecyl alcohol having about 15 oxyethylene units.

20. A composition comprising a solid, water-soluble complex comprising:
  a) a polysiloxane of the formula:

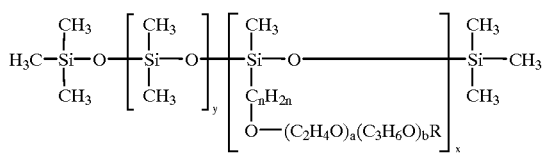

wherein n is from 2 to 6; a is from 8 to 25; and b is from 0 to 25; and the oxyalkylene groups may be random or block mixtures; y is from 0 to 5; x is from 1 to 5; and R is selected from the group consisting of hydrogen, $C_1$–$C_4$ alkyl, and a $C_1$–$C_4$ alkyl ester; or

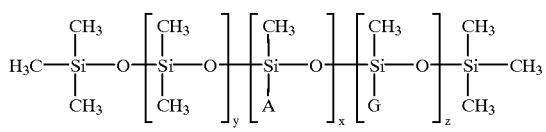

wherein A is a linear or branched alkyl having 6 to 30 carbon atoms; G is a glycol moiety of the formula —R'(OCH$_2$CH$_2$)$_m$OR" wherein R' is a divalent alkylene group having 2 to 6 carbon atoms; R" is selected from the group consisting of hydrogen, $C_1$–$C_4$ alkyl, and a $C_1$–$C_4$ alkyl ester; m is 8 to 100; y is 0 to 5; X is 0.1 to 2.5; and z is 0.1 to 5.0;
  b) a complex-forming agent of the formula:

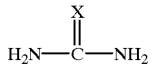

wherein X is O, S, Se, or Te,
  c) a readily clathratable polyoxyethylene selected from the group of ethoxylated fatty alcohols, ethoxylated fatty acids, and ethoxylated alkylphenols, each having at least 8 oxyethylene units per alcohol or acid group and polyoxyethylene homopolymers, optionally started with a lower alkanol, having at least about 8 oxyethylene units and block copolymers of ethylene oxide and propylene oxide, provided the block copolymer has at least about 8 oxyethylene units and a molar ratio of oxyethylene units to oxypropylene units of greater than about 0.87:1, and
  d) a non-clathratable polyoxyethylene.

21. The composition of claim 20 wherein said non-clathratable polyoxyethylene is selected from the group of polyoxyethylene homopolymers, optionally started with a lower alkanol, having less than about 8 oxyethylene units, block copolymers of ethylene oxide and propylene oxide, provided the block copolymer has less than about 8 oxyethylene units or a molar ratio of oxyethylene units to oxypropylene units of at most about 1.04:1, and ethoxylated fatty alcohols, ethoxylated fatty acids, or ethoxylated alkylphenols having less than about 8 oxyethylene units per alcohol or acid group.

22. The composition of claim 21 wherein said non-clathratable polyoxyethylene is a block copolymer of ethylene oxide and propylene oxide having a ratio of ethylene oxide to propylene oxide of at most about 1.0:1.

23. The composition of claim 21 wherein said non-clathratable polyoxyethylene is a block copolymer of ethylene oxide and propylene oxide having a ratio of ethylene oxide to propylene oxide of at most about 0.90:1.

24. The composition of claim 20 wherein the polysiloxane is of the formula:

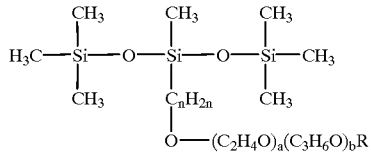

wherein n is 3; a is about 8 to about 15; and b is 0.

25. The composition of claim 24 wherein the polysiloxane is present up to 40 weight percent based on the total weight of the complex.

26. The composition of claim 24 wherein R is —CH$_3$ and a is about 8.

27. The composition of claim 24 wherein the complex-forming agent is urea.

28. The composition of claim 20 wherein the amount of the non-clathratable polyoxyethylene as a percentage of the weight of the complex is from about 5% to about 40%.

29. The composition of claim 20 wherein the amount of the non-clathratable polyoxyethylene as a percentage of the weight of the complex if from about 10% to about 15%.

30. The composition of claim 20 wherein the amount of the non-clathratable polyoxyethylene as a percentage of the weight of the complex is from about 11% to about 14%.

31. The composition of claim 20 wherein the amount of said polysiloxane as a percentage of the weight of the complex is from 5% to about 40%, the amount of said complex-forming agent as a percentage of the weight of the complex is from 30% to about 70%, the amount of the readily clathratable polyoxyethylene as a percentage of the weight of the complex is from about 10% to about 40%, and the amount of non-clathratable polyoxyethylene as a percentage of the weight of the complex is from about 5% to about 40%.

32. The composition of claim 20 wherein the amount of said polysiloxane as a percentage of the weight of the complex is from 10% to about 15%, the amount of said complex-forming agent as a percentage of the weight of the complex is from 40% to about 60%, the amount of the readily clathratable polyoxyethylene as a percentage of the weight of the complex is from about 20% to about 30%, and the amount of non-clathratable polyoxyethylene as a percentage of the weight of the complex is from about 10% to about 15%.

33. The composition of claim 20 wherein the amount of said polysiloxane as a percentage of the weight of the complex is from 11% to about 14%, the amount of said complex-forming agent as a percentage of the weight of the complex is from 45% to about 55%, the amount of the readily clathratable polyoxyethylene as a percentage of the weight of the complex is from about 22% to about 26%, and the amount of non-clathratable polyoxyethylene as a percentage of the weight of the complex is from about 11% to about 14%.

34. The composition of claim 20 wherein said readily clathratable polyoxyethylene has from about 9 to about 24 oxyethylene units per alcohol or acid group.

35. The composition of claim 20 wherein said readily clathratable polyoxyethylene is an ethoxylated fatty alcohol or fatty acid having predominantly on a weight basis of from about 8 to about 24 carbon atoms in the fatty chain.

36. The composition of claim 20 wherein said readily clathratable polyoxyethylene is an ethoxylated fatty alcohol or fatty acid having predominantly on a weight basis of from about 12 to about 18 carbon atoms in the fatty chain.

37. A composition comprising a solid, water-soluble complex comprising:
a) a polysiloxane of the formula:

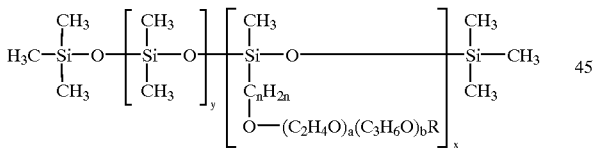

wherein n is from about 2 to about 6; a is from about 8 to about 25; and b is from 0 to about 25; and the oxyalkylene groups may be random or block mixtures; y is from 0 to about 5; x is from 1 to about 5; and R is selected from the group consisting of hydrogen, $C_1$–$C_4$ alkyl, and a $C_1$–$C_4$ alkyl ester;
b) urea, and
c) a readily clathratable polyoxyethylene selected from the group of ethoxylated fatty alcohols, ethoxylated fatty acids, and ethoxylated alkylphenols, each having at least 8 oxyethylene units per alcohol or acid group and polyoxyethylene homopolymers, optionally started with a lower alkanol, having at least about 8 oxyethylene units and block copolymer of ethylene oxide and propylene oxide, provided the block copolymer has at least about 8 oxyethylene units and a molar ratio of oxyethylene units to oxypropylene units of greater than about 1.04:1.

38. The composition of claim 37 wherein y is 0, x is about one, R is —$CH_3$ and a is about 8.

39. A composition comprising a solid, water-soluble complex comprising:
a) from about 5% to about 40% by weight of the complex of a polysiloxane of the formula:

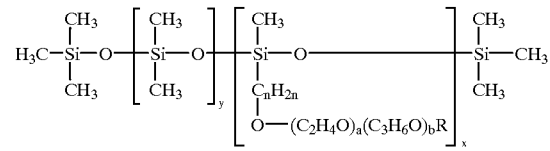

wherein n is from about 2 to about 6; a is from about 8 to about 11; and b is from 0 to about 25; and the oxyalkylene groups may be random or block mixtures; y is from 0 to about 5; x is from about 1 to about 5; and R is selected from the group consisting of hydrogen, $C_1$–$C_4$ alkyl, and a $C_1$–$C_4$ alkyl ester;

b) from about 30% to about 70% by weight of the complex of urea, c) from about 20% to about 30% by weight of the complex of a readily clathratable polyoxyethylene selected from the group ethoxylated fatty alcohols, ethoxylated fatty acids, and ethoxylated alkylphenols, each having at least 8 oxyethylene units per alcohol or acid group and polyoxyethylene homopolymers, optionally started with a lower alkanol, having at least about 8 oxyethylene units and block copolymers of ethylene oxide and propylene oxide, provided the block copolymer has at least about 8 oxyethylene units and a molar ratio of oxyethylene units to oxypropylene units of greater than about 1.04:1, and d) from about 5% to about 40% by weight of a non-clathratable polyoxyethylene selected from the group of polyoxyethylene homopolymers, optionally started with a lower alkanol, having less than about 8 oxyethylene units, block copolymers of ethylene oxide and propylene oxide, provided the block copolymer has less than about 8 oxyethylene units or a molar ratio of oxyethylene units to oxypropylene units of at most about 0.87:1, and ethoxylated fatty alcohols, ethoxylated fatty acids, or ethoxylated alkylphenols having less than about 8 oxyethylene units per alcohol or acid group.

40. The composition of claim 39 wherein "a" is from about 8 to about 10.

41. The composition of claim 40 wherein n is 3, b is zero, y is 1, x is 1, and R is methyl.

42. The composition of claim 41 wherein "a" is 8.

43. The composition of claim 42 wherein said readily clathratable polyoxyethylene is an ethoxylated tridecyl alcohol having about 15 oxyethylene units.

44. The composition of claim 43 wherein said non-clathratable is a block copolymer of ethylene oxide and propylene oxide having a molar ratio of oxyethylene units to oxypropylene units of at most about 0.87:1.

45. The composition of claim 44 wherein said readily clathratable polyoxyethylene is present in an amount of about 22% to about 26% by weight of said complex, said polysiloxane is present in an amount of about 11% to about 14% by weight of said complex, and said non-clathratable polyoxyethylene is present in an amount of about 11% to about 14% by weight of said complex.

* * * * *